United States Patent [19]

Wolf

[11] 4,080,192
[45] Mar. 21, 1978

[54] SUBSTITUTED BICYCLIC TRIAZINES

[75] Inventor: Anthony David Wolf, Newark, Del.

[73] Assignee: E. I. Du Pont de Nemours and Company, Wilmington, Del.

[21] Appl. No.: 787,606

[22] Filed: Apr. 14, 1977

[51] Int. Cl.$^2$ .................... C07D 253/08; A01N 9/22; A01N 9/12
[52] U.S. Cl. ........................................ 71/93; 544/183
[58] Field of Search ............................ 544/183; 71/93

[56] References Cited

U.S. PATENT DOCUMENTS 3,459,750  8/1969  Hardtmann ..................... 544/183

*Primary Examiner*—John M. Ford

[57] ABSTRACT

Novel compounds of formula I or II, agricultural compositions containing them, and the method of use of these compounds as general herbicides for the pre- or post-emergence control of undesired vegetation.

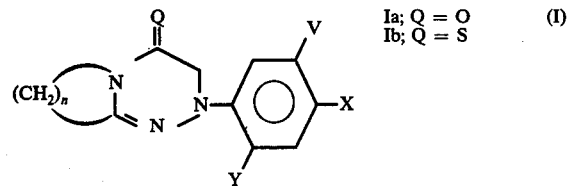

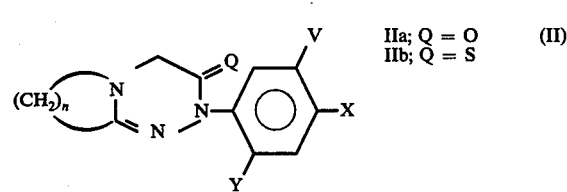

wherein:
V is hydrogen, fluorine, chlorine, bromine, methyl or —OR wherein R is alkyl of 1 to 4 carbon atoms
X is hydrogen, fluorine, chlorine, bromine, cyano, methyl, methoxy or nitro;
Y is hydrogen, fluorine, chlorine, bromine or methyl;
$n$ is 3, 4, or 5; and
Q is oxygen or sulfur.

57 Claims, No Drawings

SUBSTITUTED BICYCLIC TRIAZINES

BACKGROUND OF THE INVENTION

German Offenlegungsschrift 1,957,783 discloses amidrazones (a) and states they are useful as antihypertensives.

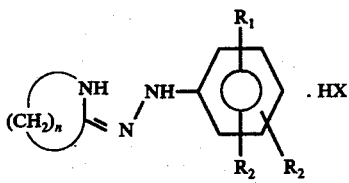

wherein $R_1$, $R_2$ and $R_3$ are hydrogen, fluorine, chlorine, bromine, trifluoromethyl or alkyl of 1–3 carbon atoms; and n is 3, 4 or 5.

Belgium Patents 802,446 and 802,447 disclose substituted arylamidrazones (b) as fungicides.

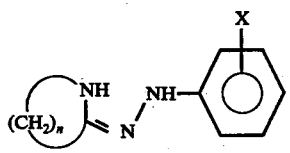

wherein X may be fluorine, chlorine, bromine, iodine, nitro, methoxy, ethoxy, methylthio, dimethylamino, trifluoromethyl or methylsulfonyl; and n may be 3, 4 or 5.

German Offenlegungsschrift 2,646,628 discloses the preparation of compounds, such as that of (c), and their use as intermediates for the preparation of herbicides.

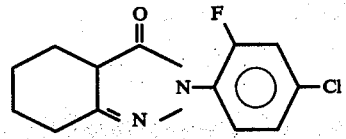

There is a continuing need for effective general herbicides so that land which has undesired vegetation growing on it may be made more suitable for growing desired crops, additionally, selective herbicides which will not destroy crops but will destroy weeds which are growing in the proximity of the crops are also needed.

DESCRIPTION OF THE INVENTION

This invention relates to novel triazines of Formula I and Formula II, to agricultural compositions containing them, and to the method of use of these compounds as general and specific herbicides for the pre- or post-emergence control of undesired vegetation.

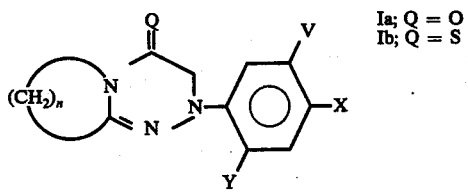

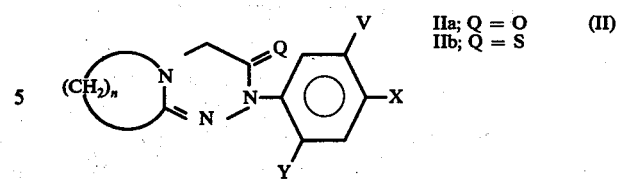

wherein:
V is hydrogen, fluorine, chlorine, bromine, methyl or —OR wherein R is alkyl of 1 to 4 carbon atoms;
X is hydrogen, fluorine, chlorine, bromine, cyano, methyl, methoxy or nitro;
Y is hydrogen, fluorine, chlorine, bromine or methyl;
n is 3, 4, or 5; and
Q is oxygen or sulfur.

Preferred for high herbicidal activity or favorable cost or both, are those compounds of Formula I or II where, independently,
1) V is hydrogen, chlorine, bromine or —OR; or
2) X is fluorine, chlorine or bromine; or
3) Y is fluorine, chlorine, bromine or methyl; or
4) n is 4 or 5; or
5) Q is oxygen.

More preferred, for their higher herbicidal activity or favorable cost or both, are those compounds of Formulas I or II where, independently,
1) V is hydrogen, chlorine, or —OR; or
2) X is chlorine or bromine; or
3) Y is fluorine, chlorine or bromine; or
4) n is 4.

Most preferred, for their excellent herbicidal activity or more favorable cost or both, are those compounds of Formulas I or II
wherein:
Q is oxygen,
V is hydrogen, chlorine or —OR,
X is chlorine or bromine,
Y is fluorine, chlorine or bromine, and
n is 4.

Specifically preferred for their outstanding herbicidal activity or highly favorable cost or both are:

1. 2-(2,4-Dichlorophenyl)-2,3,6,7,8,9-hexahydro-4H-pyrido[2,1-c][1,2,4]triazin-4-one, oil;
2. 2-(4-Chloro-2-fluorophenyl)-2,3,6,7,8,9-hexahydro-4H-pyrido[2,1-c][1,2,4]triazin-4-one, m.p. 89°–90° C;
3. 2-(2,4-Dichloro-5-methoxyphenyl)-2,3,6,7,8,9-hexahydro-4H-pyrido[2,1-c][1,2,4]triazin-4-one, m.p. 185°–187° C;
4. 2-[2,4-Dichloro-5-(1-methoxyethoxy)phenyl]-2,3,6,7,8,9-hexahydro-4H-pyrido[2,1-c][1,2,4]triazin-4-one, m.p. 162°–163° C;
5. 2-(2,4-Dichlorophenyl)-6,7,8,9-tetrahydro-4H-pyrido-[2,1-c][1,2,4]triazin-3[2H]-one, m.p. 115°–117° C;
6. 2-(4-Chloro-2-fluorophenyl)-6,7,8,9-tetrahydro-4H-pyrido-[2,1-c][1,2,4]triazin-3[2H]-one, m.p. 80°–85° C;
7. 2-(2,4-Dichloro-5-methoxyphenyl)-6,7,8,9-tetrahydro-4H-pyrido[2,1-c][1,2,4]triazin-3[2H]-one; and
8. 2-[2,4-Dichloro-5-(1-methylethoxy)phenyl]-6,7,8,9-tetrahydro-4H-pyrido[2,1-c][1,2,4]triazin-3[2H]-one, oil.

DETAILED DESCRIPTION OF THE INVENTION

In the following detailed description those compounds of Formula I wherein Q = O are referred to as Ia and those formulas of Formula I wherein Q = S are referred to as Ib. Those compounds of Formula II wherein Q = O are referred to as IIa and those compounds of Formula II wherein Q = S are referred to as IIb.

The preparation of the comounds of formula Ia is shown in equation A.

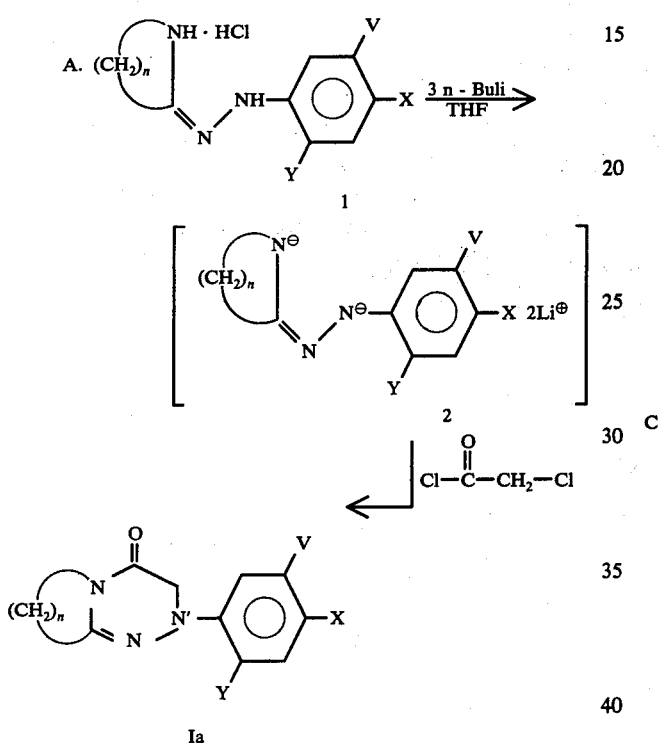

The preparation of the amidrazone acid salt 1 is achieved by methods known in the art, e.g. Ger. Offlegen. 1,957,783, Ger. Offlegen. 2,235,113 and Ger. Offlegen. 2,235,177.

The conversion of the amidrazone acid salts 1 to the dianion 2 is accomplished in a suitable solvent, e.g. tetrahydrofuran with a strong base, e.g., n-butyllithium or sodium hydride. The dianion 2 is not isolated but is treated directly with an equivalent amount of chloroacetyl chloride. After stirring the reaction mass for several hours it is poured into water and extracted with a suitable solvent, e.g., diethyl ether or methylene chloride. The organic extract of the product is dried by addition of a drying agent, e.g. anhydrous sodium sulfate and the solvent is removed by distillation or evaporation under reduced pressure leaving the crude product. Purification of the crude product is accomplished by standard techniques such as crystallization or chromatography.

The compounds of Formula Ib may be prepared by treatment of the compounds of Formula Ia with reagents capable of converting an amide to a thioamide, e.g. phosphorus pentasulfide.

The compounds of Formula IIa are prepared as shown in equations B–E.

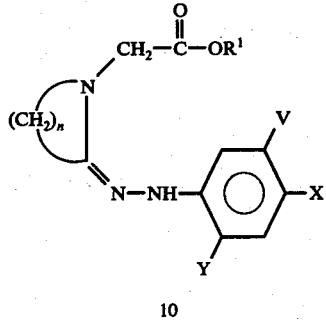

10

E

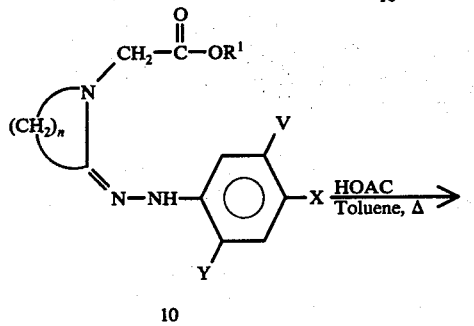

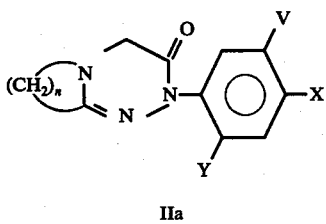

IIa

Using standard procedures the lactams 3 may be alkylated. For example, treatment of 3 with a strong base, e.g. sodium hydride in a suitable solvent, e.g. dimethylformamide produces the anion 4. The anion 4 is not isolated but it is reacted with an equivalent amount of a α-halo-ester 5 wherein X is chlorine or bromine and $R^1$ is an alkyl group of one to three carbons. The reaction mixture is stirred for a period of several hours. The reaction mass is poured into water and the product is isolated by extraction into a solvent, e.g., methylene chloride. The solution of the product is dried over a drying agent, e.g., anhydrous sodium sulfate and it is then filtered to remove the drying agent. The crude product is obtained by removal of the solvent at a reduced pressure of 50–300 mm. Pure lactam esters 6 are obtained by vacuum distillation. (Equation B)

The lactam esters 6 are then treated in an appropriate solvent, e.g. methylene chloride or chloroform with a strong alkylating agent, e.g., methyl fluorosulfate 7 (because of the suspected acute toxicity of methyl fluorosulfate extreme care must be exercised in handling this material) for a period of 1 to 2 days to form the intermediate oxonium fluorosulfates 8. (Equation C) The intermediates 8 are not isolated but they are reacted in situ with the appropriate hydrazine 9 for a period of 1 to 5 hours. (Equation D)

The amidrazone ester products 10 of this reaction are isolated by pouring the reaction mass over ice and basifying the solution with sodium or potassium hydroxide to a pH of 8–12. The reaction mass is extracted with a suitable solvent, e.g. methylene chloride. The organic extract of the product is dried with a drying agent, e.g. anhydrous sodium sulfate and then filtered. The solvent is removed under reduced pressure (15–300 mm) with a rotary evaporator leaving the crude product 10. Further purification of 10 is accomplished by standard techniques, e.g. chromatography or crystallization. In most cases the crude product 10 is used directly in the next step (Equation E) without further purification.

The compounds, IIa, of this invention are obtained by refluxing a solution of 10 for a period of one to forty-eight hours in an appropriate solvent, e.g. toluene with a catalytic amount of acid, e.g. acetic acid. After the reaction is complete the solvent is removed by distillation. The crude product IIa thus obtained is further purified by standard techniques, e.g. chromatography or crystallization.

The compounds of Formula IIb may be prepared by treatment of the compounds of Formula IIa with reagents capable of converting an amide into a thioamide, e.g. phosphorus pentasulfide.

The following example further illustrates the preparation of the compounds of this invention.

EXAMPLE I

Preparation of
2(2,4-dichlorophenyl)-2,3,6,7,8,9-hexahydro-4H-Pyrido-[2,1-c]-[1,2,4]triazin-4-one 6.0 parts of 2-piperidone-2,4-dichlorophenylhydrazone hydrochloride, prepared by methods similar to those described in Ger. Offlegen. 2,235,113 and 2,235,177, were combined with 200 parts of dry tetrahydrofuran and cooled to −10° C under an atmosphere of nitrogen. To this solution 25.5 parts of a solution of n-butyllithium in hexane (purchased from Foote Mineral Co., Exton, Pa.) were added dropwise while maintaining the temperature of the reaction between −10° and +10° C. The reaction mass was stirred for about 15 minutes following the addition of the n-butyllithium. 2.4 parts of chloroacetyl chloride were then added dropwise while maintaining the temperature between −10° and +10° C. After the addition of chloroacetylchloride was complete, the reaction mass was allowed to warm to room temperature. It was then stirred for 2 hours. The crude reaction mass was poured into 500 parts of water. The aqueous solution was extracted three times with 200 parts of methylene chloride. The crude extracts were combined and dried over anhydrous sodium sulfate and then filtered. The solvent was removed by evaporation under reduced pressure of 50 to 300 mm on a rotary evaporator. The crude product was purified by dry column chromatography on alumina with benzene. 0.9 parts of an oil was obtained with I.R. bands at 1700 $cm^{-1}$, 1680 $cm^{-1}$, 970 $cm^{-1}$ and 912 $cm^{-1}$.

Using a procedure analogous to Example I with the appropriate amidrazone base, and chloroacetyl chloride, the following compounds of Formula Ia may be prepared.

| n | Y | X | V | Q |
|---|---|---|---|---|
| 4 | H | Cl | H | O |
| 4 | F | Cl | H | O |
| 4 | CH₃ | Cl | H | O |
| 4 | Cl | Cl | —OCH₃ | O |
| 4 | Cl | Cl | —OCH₂CH₃ | O |
| 4 | Cl | Cl | —OCH(CH₃)₂ | O |
| 5 | Cl | Cl | —O(—CH₂)₂CH₃ | O |
| 5 | Cl | Cl | —OCH₂CH(CH₃)₂ | O |
| 5 | Cl | Cl | —OCH(CH₃)CH₂CH₃ | O |
| 5 | Br | Br | H | O |
| 4 | H | H | H | S |
| 3 | F | F | F | O |
| 5 | H | CH₃ | H | O |
| 5 | F | CH₃O | H | O |
| 5 | Cl | Cl | Cl | O |

-continued

| n | Y | X | V | Q |
|---|---|---|---|---|
| 3 | H | Br | H | O |
| 4 | F | Br | H | O |
| 4 | Cl | Cl | Br | O |
| 5 | F | CN | H | O |
| 5 | F | NO$_2$ | H | O |
| 4 | Cl | Cl | CH$_3$ | S |
| 4 | Cl | Cl | —O(CH$_2$)$_3$CH$_3$ | O |
| 4 | Br | Br | —OCH$_3$ | O |
| 4 | Br | Br | —OCH(CH$_3$)$_2$ | O |
| 4 | F | F | —OCH$_3$ | O |
| 4 | F | F | —OCH(CH$_3$)$_2$ | O |
| 4 | CH$_3$ | CH$_3$ | H | O |
| 4 | CH$_3$ | CH$_3$ | —OCH$_3$ | O |

EXAMPLE 2

Preparation of
2-(2,4-dichlorophenyl)-6,7,8,9-tetrahydro-4H-Pyrido-[2,1-c][1,2,4]triazin-3(2H)-one a) Preparation of Ethyl 2-oxo-1-piperidineacetate 9.9 parts of δ-valerolactam (purchased from Aldrich Chemical Co., Milwaukee, Wisc. 53233) were dissolved in 100 part of dimethylformamide. To this solution was added 4.8 parts of a 50% dispersion of sodium hydride in mineral oil (purchased from Callgary Chemical Company, Callgary, Pa.). The reaction mixture was stirred for a period of 30 minutes. To the above reaction mixture 16.7 parts of ethylbromoacetate was added dropwise keeping the temperature less than 25° C during the addition. After the addition was completed, the reaction was stirred at room temperature for an additional 30 minutes. The reaction mass was poured into 200 parts of water. The product was isolated by extraction from the aqueous solution with three successive 200-part portions of methylene chloride. The combined organic extracts of the product were dried with anhydrous sodium sulfate. The solution of the product was filtered and the solvent was removed by evaporation at a reduced pressure of 50-300 mm on a rotary evaporator. The crude product obtained was further purified by vacuum distillation at 115°-120° C at 1.5 mm; 8.2 parts of product were obtained.

b) Preparation of ethyl-2-(2,4-dichlorophenylhydrazono)-1-piperidineacetate.

18.5 parts of ethyl 2-oxo-1-piperidineacetate, 300 parts of methylene chloride and 12.0 parts of methyl fluorosulfate were combined and stirred at room temperature for 24 hours.

A solution of 17.7 parts of 2,4-dichlorophenylhydrazine in methylene chloride was added dropwise to the above reaction mixture containing [1-(2-ethoxy-2-oxoethyl)piperidin-2-ylidene]methyloxonium fluorosulfate while keeping the temperature of the reaction less than 30° C. After the addition was completed the reaction was stirred for an additional 30 minutes. The reaction mass was then poured into 1000 parts of water. The pH was raised to 12.0 with 20% potassium hydroxide solution. The crude product was extracted with three successive portions of 1000 parts of methylene chloride. The organic extracts of the product were dried over anhydrous sodium sulfate. The solution of the product was filtered to remove the drying agent. The solvent was removed at a reduced pressure of 50-300 mm with a rotary evaporator leaving the crude product which was used in the next step without further purification.

c) Preparation of 2-(2,4-dichlorophenyl)-6,7,8,9-tetrahydro-4H-Pyrido[2,1-c][1,2,4]triazine-3(2H)-one.

The crude product from b was combined with 400 parts of toluene and 2 parts of glacial acetic acid. The mixture was refluxed for 12 hours. The crude product was obtained by removal of the solvent at a reduced pressure at 50-300 mm on a rotary evaporator. Further purification of the product was accomplished by dry column chromatography on silica gel (purchased from ICN Pharmaceuticals, Inc., Cleveland, Ohio) with 7% ethanol in chloroform. 8.0 parts of product with m.p. 115°-117° C were obtained after chromatography.

Using a procedure analogous to Example 2 with the appropriate hydrazone lactam ester the following compounds of Formula IIa may be prepared.

| n | Y | X | V | Q |
|---|---|---|---|---|
| 4 | H | Cl | H | O |
| 4 | F | Cl | H | O |
| 4 | CH$_3$ | Cl | H | O |
| 4 | Cl | Cl | OCH$_3$ | O |
| 4 | Cl | Cl | OCH$_2$CH$_3$ | O |
| 4 | Cl | Cl | OCH(CH$_3$)$_2$ | O |
| 5 | Br | Br | H | O |
| 5 | Cl | Cl | O(CH$_2$)$_3$CH$_3$ | O |
| 5 | Cl | Cl | O(CH$_3$)CH$_2$CH$_3$ | O |
| 5 | Cl | Cl | OCH(CH$_3$)CH$_2$CH$_3$ | O |
| 4 | H | H | H | S |
| 3 | F | F | F | O |
| 5 | H | CH$_3$ | H | O |
| 5 | F | CH$_3$O | H | O |
| 5 | Cl | Cl | Cl | O |
| 3 | H | Br | H | O |
| 4 | F | Br | H | O |
| 4 | Cl | Cl | Br | O |
| 5 | F | CN | H | O |
| 5 | F | NO$_2$ | H | O |
| 4 | Cl | Cl | CH$_3$ | O |
| 4 | Cl | Cl | O(CH$_2$)$_3$CH$_3$ | O |
| 4 | Br | Br | OCH$_3$ | O |
| 4 | Br | Br | —OCH(CH$_3$)$_2$ | O |
| 4 | F | F | OCH$_3$ | O |
| 4 | F | F | —OCH(CH$_2$)$_2$ | O |
| 3 | CH$_3$ | —OCH$_3$ | —OCH(CH$_3$)$_2$ | O |

FORMULATIONS

Useful formulations of the compounds of Formula I and II include dusts, granules, pellets, solutions, suspensions, emulsions, wettable powders, emulsifiable concentrates and the like. Many of these compounds can be applied directly. Sprayable formulations can be extended in suitable media and used at spray volumes of from a few liters to several hundred liters per hectare. High strength compositions are used primarily for preparing more dilute field strength formulations. The formulations, broadly, contain about 0.05% to 99% by weight of active ingredient(s) and at least one of (a) about 0.1% to 20% surfactant(s) and (b) about 1% to 99.95% solid or liquid diluent(s). More specifically, they will usually contain these ingredients in the following approximate proportions:

| | Percent by Weight | | |
|---|---|---|---|
| | Active Ingredient | Diluent(s) | Surfactant(s) |
| Wettable Powders | 5-90 | 1-94 | 1-10 |
| Oil Suspensions, Emulsions, Solutions (including Emulsifiable Concentrates) | 5-50 | 40-95 | 0-15 |
| Aqueous Suspensions | 5-50 | 40-94 | 1-20 |

|  | Percent by Weight | | |
| --- | --- | --- | --- |
|  | Active Ingredient | Diluent(s) | Surfactant(s) |
| Dusts | 0.05–25 | 70–99.95 | 0–5 |
| Granules and Pellets | 0.05–95 | 1–99.95 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd Edn., Dorland Books, Caldwell, N.J. Suitable diluents include finely divided or granular solids classified as attapulgites, botanicals, calcites, diatomites, dolomites, gypsum, kaolinites, limestones, mica, montmorillonoids, phosphates, pyrophyllites, sulfur, sand, talcs, tripolites, vermiculite, and synthetics. These synthetics can include precipitated hydrated silicon dioxide, precipitated hydrated calcium silicate, precipitated calcium carbonate and synthetic organics. The more absorptive diluents are preferred for wettable powders and the denser ones for dusts. Typical liquid diluents and solvents are described in Marsden, "Solvents Guide," 2nd Edn., Interscience, New York, 1950. Solubility under 0.1% is preferred for suspension concentrates; solution concentrates are preferably stable against phase separation at 0° C. "McCutcheon's Detergents and Emulsifiers 1975 Annual," MC Publ. Corp., Ridgewood, New Jersey, as well as Sisely and Wood, "Encyclopedia of Surface Active Agents," Chemical Publ. Co., New York, 1964, list surfactants and recommended uses. All formulations can contain minor amounts of additives to reduce foam, caking, corrosion, microbiological growth, etc., or to mark visually the area that has been treated.

Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

Granules may be made in several ways. For example, the active ingredient may be sprayed onto preformed granular carriers. Suitable preformed granular carriers include those suitable diluents listed earlier having a particle size range from USS Sieve No. 200 (74 microns) to USS Sieve No. 10 (2,000 microns). The preferred particle size is from USS Sieve No. 140 (105 microns) to USS Sieve No. 20 (840 microns). Depending upon the nature of the carrier, the active ingredient may remain on the surface of the carrier or be absorbed into the carrier. Usually when the active ingredient remains on the surface of the carrier, a binding agent is used to hold the active ingredient on the surface. The binding agent should bind the active ingredient to the surface well enough so that not more than 10% of the active is removed during normal shipping and handling operations. Suitable binding agents include materials which are at least partially soluble in any liquid used in the manufacture of the granules and which adhere to the granular surface. Water-soluble binders are preferred. Suitable binders include, but are not limited to, water-soluble polymers such as polyvinylalcohols of molecular weights from about 20,000 to about 150,000; polyvinylpyrrolidones of molecular weights from about 20,000 to about 100,000; and polyoxyethylenes of molecular weights from about 100,000 to about $6 \times 10^6$. Other suitable binders include ligninsulfonates, starches, sugars and certain surface active agents listed in "McCutcheons' Detergents and Emulsifiers 1975 Annual," Mc Publ. Corp., Ridgewood, New Jersey.

The active may be sprayed as a solution in a suitable solvent, which may or may not be removed from the formulation. If the active ingredient is a liquid, it may be sprayed onto or mixed with the carrier directly. If it is a solid, it may be melted and applied directly as a liquid. If very low strength granules are desired, the active may be vaporized onto the carrier. Granules may also be prepared by agglomeration techniques. For example, the active ingredient and a finely divided solid diluent may be mixed and agglomerated by techniques known in the art such as spraying with a liquid in a fluidized bed or pan granulator. The active ingredient and diluent may also be mixed with other formulation ingredients and pelletized. The pellets may then be crushed to a desired granular size. Pellets may be made by agglomeration techniques. See J. E. Browning, "Agglomeration," Chemical Engineering, Dec. 4, 1967, pp. 147ff. and "Perry's Chemical Engineer's Handbook," 4th. Edn., McGraw-Hill, N.Y., 1963, pp. 8-59ff.

For further information regarding the art of formulation, see for example:

- H. M. Loux, U.S. Pat. No. 3,235,361, Feb. 15, 1966, Col. 6, line 16 through Col. 7, line 19 and Examples 10 through 41.
- R. W. Luckenbaugh, U.S. Pat. No. 3,309,192, Mar. 14, 1967, Col. 5, line 43 through Col. 7, line 62 and Ex. 8, 12, 15, 39, 41, 52, 53, 58, 132, 138–140, 162–164, 166, 167, 169–182.
- H. Gysin and E. Knusli, U.S. Pat. No. 2,891,855, June 23, 1959, Col. 3, line 66 through Col. 5, line 17 and Examples 1–4.
- G. C. Klingman, "Weed Control as a Science," John Wiley & Sons, Inc., New York, 1961 pp. 81–96.
- J. D. Fryer and S. A. Evans, "Weed Control Handbook," 5th Edn. Blackwell Scientific Publications, Oxford, 1968, pp. 101–103.

In the following examples, all parts are by weight:

EXAMPLE 3

Wettable Powder

| | |
| --- | --- |
| 2-(4-chloro-2-fluorophenyl)-2,3,6,7,8,9-hexahydro-4H-pyrido[2,1-c]-[1,2,4]-triazin-4-one | 25% |
| sodium ligninsulfonate | 2% |
| sodium alkylnaphthalenesulfonate | 2% |
| synthetic amorphous silica | 3% |
| kaolinite | 68% |

The ingredients are blended thoroughly, ground in an air mill to produce an average particle size under 15 microns, reblended and sifted through a U.S.S. No. 50 sieve (0.3 mm openings) before packaging.

EXAMPLE 4

Solution

| | |
| --- | --- |
| 2-(2,4-dichlorophenyl)-2,3,6,7,8,9-hexahydro-4H-pyrido[2,1-c]-[1,2,4]-triazin-4-one | 20% |

| -continued | |
|---|---|
| Solution | |
| dimethylformamide | 80% |

The ingredients are combined and stirred to produce a solution, which can be used for low-volume applications.

EXAMPLE 5

| Extruded Pellet | |
|---|---|
| 2-(2,4-dichloro-5-methoxyphenyl)-2,3,6,7,8,9-hexahydro-4H-pyrido[2,1-c]-[1,2,4]-triazin-4-one | 1% |
| anhydrous sodium sulfate | 10% |
| crude calcium ligninsulfonate | 5% |
| sodium alkylnaphthalenesulfonate | 1% |
| polyoxyethylene (4 × 10$^6$ average molecular weight) | 1% |
| calcium/magnesium bentonite | 82% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled. All componds of this invention may be formulated in this manner.

EXAMPLE 6

| Emulsifiable Concentrate | |
|---|---|
| 2-(2,4-dichlorophenyl)-2,3,6,7,8,9-hexahydro-4H-pyrido[2,1-c]-[1,2,4]-triazin-4-one | 25% |
| blend of oil soluble sulfonates and polyoxyethylene ethers | 4% |
| xylene | 71% |

The ingredients are combined and stirred until solution is complete. A fine screen filter is included in packaging operation to insure the absence of any extraneous undissolved material in the product.

EXAMPLE 7

| Aqueous Suspension | |
|---|---|
| 2-[2,4-dichloro-5-(1-methylethoxy)phenyl]-2,3,6,7,8,9-hexahydro-4H-pyrido[2,1-c]-[1,2,4]-triazin-4-one | 50.0% |
| polyacrylic acid thickener | 0.3% |
| dodecylphenol polyethylene glycol ether | 0.5% |
| disodium phosphate | 1.0% |
| monosodium phosphate | 0.5% |
| polyvinylalcohol | 1.0% |
| pentachlorophenol | 0.4% |
| water | 46.3% |

The ingredients are ground together in a sand mill to produce particles essentially all under 5 microns in size.

EXAMPLE 8

| Wettable Powder | |
|---|---|
| 2-(2,4-dichloro-5-methoxyphenyl)-2,3,6,7,8,9-hexahydro-4H-pyrido[2,1-cA]-[1,2,4]-triazin-4-one | 50% |
| sodium alkylnaphthalenesulfonate | 2% |
| sodium ligninsulfonate | 2% |
| synthetic amorphous silica | 3% |

| -continued | |
|---|---|
| Wettable Powder | |
| kaolinite | 43% |

The ingredients are thoroughly blended, passed through an air mill to produce an average particle size under 15 microns, reblended and sifted through a U.S.S. No. 50 sieve (0.3 mm openings) before packaging.

EXAMPLE 9

| High-Strength Concentrate | |
|---|---|
| 2-(4-chloro-2-fluorophenyl)-2,3,6,7,8,9-hexahydro-4H-pyrido[2,1-c]-[1,2,4]-triazin-4-one | 99% |
| trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

EXAMPLE 10

| Low Strength Granule | |
|---|---|
| 2-(2,4-dichlorophenyl)-2,3,6,7,8,9-hexahydro-4H-pyrido[2,1-c]-[1,2,4]-triazin-4-one | 0.5% |
| attapulgite granules (low volatile matter); 0.59–0.25 mm, i.e., U.S.S. #30–60 mesh size | 99.5% |

Forty grams of a solution containing 2.5% 2-(2,4-dichlorophenyl)-2,3,6,7,8,9-hexahydro-4-pyrido[2,1-c]-[1,2,4]-triazin-4-one dissolved in methyl alcohol are slowly atomized onto a fluidized bed of attapulgite granules (199 gm). Fluidization of the granules is continued after atomization is complete and until all the methyl alcohol is evaporated from the granules. The granules are packaged for use.

EXAMPLE 11

| Extruded Pellet | |
|---|---|
| 2-(4-chloro-2-fluorophenyl)-2,3,6,7,8,9-hexahydro-4H-pyrido[2,1-c]-[1,2,4]-triazin-4-one | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and moistened with about 10–12% water. The mixture is then extruded as cylinders about 3 mm in diameter which are cut to be about 3 mm long. These pellets may be used directly after drying or the dried pellets may be crushed to pass a U.S.S. No. 20 sieve (0.84 mm openings). The pellets retained on a U.S.S. No. 40 sieve (0.42 mm openings) may be packaged for use and the fines recycled.

EXAMPLE 12

| Low Strength Granule | |
|---|---|
| 2-(2,4-dichloro-5-methoxyphenyl)-2,3,6,7,8,9-hexahydro-4H-pyrido[2,1-c][1,2,4]-triazin-4-one | 0.2% |
| anhydrous sodium sulfate | 10% |
| crude calcium ligninsulfonate | 5% |

| Low Strength Granule | |
|---|---|
| sodium alkylnaphthalenesulfonate | 1% |
| finely divided attapulgite clay | 83.8% |

The ingredients are blended, hammer milled and placed in a fluidized bed granulator. Water is aspirated into the fluidized bed of powder until small granules are formed. Water aspiration is then stopped but fluidization is continued to dry the formed granules. The granules are removed from the granulator and screened to pass a USS #20 sieve (0.84 mm opening). Granules retained on a USS #40 sieve (0.42 mm opening) are packaged for use. Granules larger than 0.84 mm are ground and recycled. Fined smaller than 0.42 mm are also recycled.

EXAMPLE 13

| Extruded Pellet | |
|---|---|
| 2-[2,4-dichloro-5-(1-methylethoxy)phenyl]-2,3,6,7,8,9-hexahydro-4H-pyrido[2,1-c]-[1,2,4]-triazin-4-one | 0.1% |
| anhydrous sodium sulfate | 10% |
| crude calcium ligninsulfonate | 5% |
| sodium alkylnaphthalenesulfonate | 1% |
| polyoxyethylene (4 × 10⁶ average molecular wt.) | 1% |
| calcium/magnesium bentonite | 82.9% |

The ingredients are blended, hammer milled and then moistened with about 12% water. The moist mixture is extruded as cylinders about 1 mm in diameter and about 2 mm long. These small pellets are dried and packaged. They are applied directly.

EXAMPLE 14

| Low Strength Granule | |
|---|---|
| 2-(2,4-dichlorophenyl)-2,3,6,7,8,9-hexahydro-4H-pyrido[2,1-c]-[1,2,4]-triazin-4-one | 0.05% |
| dimethylformamide | 5% |
| attapulgite granules (low volatile matter; 0.59–0.25 mm i.e. USS #30–60 mesh size) | 94.95% |

One-tenth of a gram of 2-(2,4-dichlorophenyl)-2,3,6,7,8,9-hexahydro-4H-pypido[2,1-c]-[1,2,4]-triazin-4-one is dissolved in 9.9 grams of dimethylformamide. This solution is very slowly atomized onto 190.1 grams of a rapidly tumbling bed of the attapulgite granules. After application of the active ingredient is complete, the formulation is blended for a few additional minutes. The dimethylformamide is not removed from the formulation. The granules are packaged for use.

EXAMPLE 15

| Emulsifiable Concentrate | |
|---|---|
| 2-(4-chloro-2-fluorophenyl)-2,3,6,7,8,9-hexahydro-4H-pyrido[2,1-c]-[1,2,4]-triazin-4-one | 20% |
| blend of oil-soluble sulfonate with poloxyethylene ethers | 6% |
| aromatic hydrocarbon solvent with a Tag closed cup flash point between 100 and 115° F. | 74% |

The ingredients are combined and stirred until solution is complete. The solution is filtered through a fine screen filter prior to packaging to remove any extraneous undissolved material.

EXAMPLE 16

| Low Strength Granules | |
|---|---|
| 2-(2,4-dichloro-5-methoxyphenyl)-2,3,6,7,8,9-hexahydro-4H-pyrido[2,1-c]-[1,2,4]-triazin-4-one | 0.1% |
| sodium ligninsulfonate | 5% |
| preformed sand granules having a particle size distribution from USS Sieve No. 140 (105 microns) to USS Sieve No. 50 (297 microns) | 94.9% |

0.5 gm 2-(2,4-dichloro-5-methoxyphenyl)-2,3,6,7,8,9-hexahydro-4H-pyrido[2,1-c]-[1,2,4]-triazin-4-one and 25 gm sodium ligninsulfonate are dissolved in 50 gm water. This solution is slowly sprayed onto a tumbling bed of the sand granules (474.5 gms). After spraying is complete the tumblng granules are warmed to remove the water. The resulting granules are packaged for use.

EXAMPLE 17

| Wettable Powder | |
|---|---|
| 2-(2,4-dichlorophenyl)-6,7,8,9-tetrahydro-4H-pyrido-[2,1-c][1,2,4]triazin-3[2H]-one | 25% |
| sodium ligninsulfonate | 2% |
| sodium alkylnaphthalenesulfonate | 2% |
| synthetic amorphous silica | 3% |
| kaolinite | 68& |

The ingredients are blended thoroughly, ground in an air mill to produce an average particle size under 15 microns, reblended and sifted thrugh a USS No. 50 sieve (0.3 mm openings) before packaging.

EXAMPLE 18

| Low Strength Granule | |
|---|---|
| 2-(4-chloro-2-fluorophenyl)-6,7,8,9-tetrahydro-4H-pyrido-[2,1-c][1,2,4]triazin-3[2H]-one | 0.5% |
| attapulgite granules (low volatile matter; 0.59–0.25 mm, i.e. USS #30–60 mesh size) | 99.5%. |

Forty grams of a solution containing 2.5% 2-(2,4-dichlorophenyl)-2,3,6,7,8,9-hexahydro-4-pyrido[2,1-c][1,2,4]triazin-4-one dissolved in methyl alcohol are slowly atomized onto a fluidized bed of attapulgite granules (199 gm). Fluidization of the granules is continued after atomization is complete and until all the methyl alcohol is evaporated from the granules. The granules are packaged for use.

EXAMPLE 19

| Emulsifiable Concentrate | |
|---|---|
| 2-[2,4-dichloro-5-(1-methylethoxy)phenyl]-6,7,8,9-tetrahydro-4H-pyrido[2,1-c][1,2,4]triazin-3[2H]-one | 25% |
| blend of oil soluble sulfonates and polyoxyethelene ethers | 4% |
| xylene | 71% |

The ingredients are combined and stirred until solution is complete. A fine screen filter is included in packaging operation to insure the absence of any extraneous undissolved material in the product.

The compounds of Formulae I and II can also be combined with other herbicides and are particularly useful in combination with bromacil [3-(sec-butyl)-5-bromo-6-methyluracil], diuron[3-(3,4-dichlorophenyl)-1,1-dimethylurea], 3-cyclohexyl-1-methyl-6-dimethylamino-s-triazine-2,4(1H,3H)-dione, paraquat [1,1'-dimethyl-4,4'-bipyridinum ion], m-(3,3-dimethylureido) phenyl tert-butylcarbamate, 2-methyl-4-chlorophenoxyacetic acid, its salts or esters, 4-amino-6-tert-butyl-3-methylthio-as-triazin-5(4H)-one, aryl 4-nitrophenyl ethers such as 2,4,6-trichlorophenyl 4-nitrophenyl ether and 2,4-dichlorophenyl 4-nitrophenyl ether for controlling a broad spectrum of weeds.

UTILITY

The compounds of the present invention are useful when applied as pre- and/or post-emergence treatments for broad-spectrum control of a wide variety of weed and brush species growing on industrial sites, storage lots, along fences and building foundations, along railroad and utility rights-or-way, etc. Many of the compounds are also useful for selective weed control in crops, e.g., corn, wheat and cotton. They may be applied pre- or post-emergence to the crop and/or weeds.

The precise amount of the compounds of the invention to be used in any particular situation will vary widely according to the end result desired. Factors affecting the optimum rate of application include the crop, weeds to be controlled, soil type, formulation used, prevailing weather conditions, foliage density, length of time for which residual activity is desired, etc. Broadly speaking, the compounds are used at levels of about 0.03 to 20 kilograms per hectare, preferably approximately 0.125 to 10 kilograms per hectare. In general, the higher rates of application from within this range will be selected for adverse conditions or where extended persistence in soil is desired, while the lower rates will be used for selective weed control in crops.

Herbicidal activity of the subject compounds was discovered in a number of greenhouse tests. The test procedures and results are shown in tests A, B, C and D below:

TEST A

Seeds of crabgrass (Digitaria spp.), barnyardgrass (*Echinochloa crusgalli*), wild oats (*Avena fatua*), Cassia tora, morningglory (*Ipomoea spp.*), cocklebur (*Xanthium spp.*), sorghum, corn, soybean, rice, wheat and nutsedge tubers were planted in a growth medium and treated preemergence with the chemicals dissolved in a nonphytotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, whereupon all species were compared to controls and visually rated for response to treatment. The ratings are based on a numerical scale extending from 0 = no injury, to 10 = complete kill. The accompanying descriptive symbols have the following meanings: B = burn; C = chlorosis/necrosis; D = defoliation; E = emergence inhibition; G = growth retardation and H = formative effects. The ratings for the compound tested by this procedure are shown in Table I.

TABLE I

| COMPOUND | POST EMERGENCE |
|---|---|

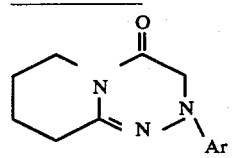

| Ar | Kg/Ha | bush bean | cotton | morning glory | cocklebur | cassia | nutsedge | crabgrass | barnyard grass | wild oats | wheat | corn | soybean | rice | sorghum |
|---|---|---|---|---|---|---|---|---|---|---|---|---|---|---|---|
| 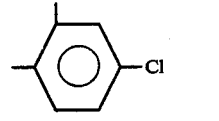 | 2 | 9B | 9B | 10B | 7B | 7B | 7B | 10B | 9B | 7B | 6B | 6B | 7B | 6B | 7B |
| 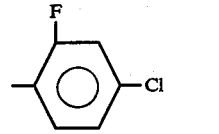 | 0.4 | 9B | 9B | 8B | 7B | 6B | 4B | 4B | 9B | 5B 7H | 2B | 5B | 8B | 7B | 7B |
| (Cl, Cl, OCH(CH₃)₂ phenyl) | 0.4 | 9B | 9B | 10B | 5B | 4B | 7B | 3B 7H | 9B | 5B 8H | 4B | 4B | 7B | 7B | 8B |

TABLE I-continued

| Ar | Kg/Ha | morning glory | cocklebur | cassia | nutsedge | crab-grass | barnyard grass | wild oats | wheat | corn | soy-bean | rice | sorghum |
|---|---|---|---|---|---|---|---|---|---|---|---|---|---|
| 2,4-Cl,Cl / 2-OCH₃ (dichloro-methoxyphenyl) | 0.4 | 9B | 9B | 10B | 3B | 2B 4H | 2B 7C | 4B 9H | 9B | 5B 7H | 4B | 4B | 5B | 7B 7B |

Ar structure (piperidine-fused triazinone, N-methyl):

| Ar | Kg/Ha | | | | | | | | | | | | |
|---|---|---|---|---|---|---|---|---|---|---|---|---|---|
| 2-F, 4-Cl phenyl | 0.4 | 8B | 7B 7D | 5B | 3B | 3B | 1B | 5B | 6B | 1B | 1B | 1B | 4B | 5B 2B |
| 2,4-dichlorophenyl | 0.4 | 5B | 7B 7D | 5B | 2B | 4B | 2B | 4B | 4B | 2B | 2B | 3B | 4B | 3B 3B |
| 3-Cl, 2-Cl, 4-OCH(CH₃)₂ phenyl | 0.4 | 9B | 9B | 9B | 6B | 5B | 3B 7C | 3B 6H | 9B | 6B | 4B | 4B | 2H 7B | 7B 8B |

COMPOUND — PRE-EMERGENCE

Structure: piperidine-fused triazinone with N–Ar

| Ar | Kg/Ha | morning glory | cocklebur | cassia | nutsedge | crab-grass | barnyard grass | wild oats | wheat | corn | soy-bean | rice | sorghum |
|---|---|---|---|---|---|---|---|---|---|---|---|---|---|
| 2,4-dichlorophenyl | 2 | 10C | 10C | — | 10C | 10C | 10C | 10C | 10C | 9C | 9H | 9C | 10C |
| 2-F, 4-Cl phenyl | 0.4 | 1C 8H | 10C | 10C | 9C | 9C | 10C | 10C | 10C | 9H | 1C 4G | 9C | 9C |
| 2,4-dichloro, 3-OCH(CH₃)₂ phenyl | 0.4 | 7H | 1H | 1C | 9C | 10C | 10C | 10C | 10C | 2C 7H | 7G | 9C | 10C |
| 2,4-dichloro, 3-OCH₃ phenyl | 0.4 | 10C | 10E | 7C | 9C | 10C | 10C | 10C | 10C | 9H | 2C 6G | 9C | 10C |

TABLE I-continued

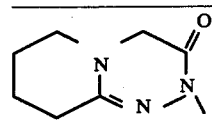

| Ar | | | | | | | | | | | | |
|---|---|---|---|---|---|---|---|---|---|---|---|---|
| 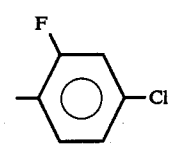 (F, Cl) | 0.4 | 8C | 1C 5H | 9C | 1C | 9C | 9C | 8C | 8C | 7C | 3C | 8C | 8C |
| 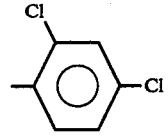 (Cl, Cl) | 0.4 | 1C 5G | 1C | 2C | 0 | 1C 9H | 9C | 8C | 8C | 6C | 3C | 7C | 7C |
| 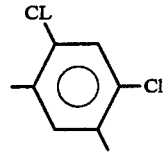 (Cl, Cl, OCH(CH₃)₂) | 0.4 | 10C | 1C 5G | 7C | 9C | 10C | 10C | 10C | 10C | 9H | 9H | 9C | 10C |

TEST B

Two plastic bulb pans were filled with fertilized and limed Fallsington silt load soil. One pan was planted with corn, sorghum and several grassy weeds. The other pan was planted with soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), giant foxtail (*Setaria faberii*), Kentucky bluegrass (*Poa pratensis*), cheatgrass (*Bromus secalinus*), mustard (*Brassica arvensis*), cocklebur (*Xanthium pennsylvanicum*), pigweed (*Amaranthus retroflexus*), curly indigo (*Aeschynomene virginica*), morningglory (*Ipomoea hederacea*), cassia (*Cassia tora*), teaweed (*Sida spinosa*), velvetleaf (*Abutilon theophrasti*), and jinsonweed (*Datura stramonium*). A 5-inch diameter plastic pot was also filled with prepared soil and planted with rice and wheat. A 4-innch pot was planted with sugarbeets. The above four containers were treated preemergence (compound sprayed on soil surface before seed germination).

Twenty-eight days after treatment, the plants were evaluated and the data below recorded.

TABLE II

| | | Fallsington Sandy Loam | | | | | | | | | |
|---|---|---|---|---|---|---|---|---|---|---|---|
| kg/ha | Rate | Crab-grass | Barn-yard-grass | Sor-ghum | Wild oats | Johnson-grass | Giants foxtail | Ky.Blue-grass | Cheat | Corn | ard | Must-ard |
|  | 1/8 | 8H | 3C | 0 | 0 | 0 | 0 | 0 | 0 | 0 | 3C | |
| | 1/2 | 10H | 6C | 3C | 6C | 6H | 2H | 7H | 3C | 2C | 9C | |

| | | Cock-lebur | H. Pig-weed | Nut-sedge | Mor-in-digo | ning glory | Cas sia | Vel Tea-weed | Jim vet-leaf | son-weed | Soy-bean | Rice | Wheat | Sugar-beets |
|---|---|---|---|---|---|---|---|---|---|---|---|---|---|---|
| 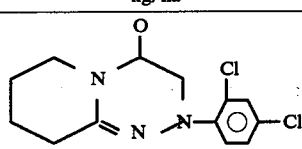 | | 0 | - | 0 | - | 0 | - | 2C | 2C | 3C | 0 | 0 | 0 | 2C |
| 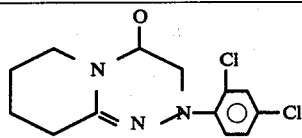 | | 3C | - | 2C | - | 0 | - | 10C | 10C | 10C | 2C | 6C | 3C | 9C |

TEST C

Table III is presented to further illustrate the biological activity of the compounds of this invention.

The test compounds were applied in a nonphytotoxic solvent to pots containing soil and seeds of an intermediate hybrid rice, japonica rice, barnyardgrass (*Echinochloa crusgalli*), morning glory (*Ipomoea sp.*), wheat, wild oats (*Avena fatua*), downy brome (*Bromus tectorum*), and cheat (*Bromus secalinus*). The plants were maintained in a greenhouse, and visual plant response ratings (as described in Table 1) were taken 3 to 5 weeks after application.

TABLE III

| COMPOUND | kg ai/ha | Preemergence | | | | | | | |
|---|---|---|---|---|---|---|---|---|---|
| | | Intermediate Rice | Japonica Rice | Barnyardgrass | Morningglory | Wheat | Wild Oats | Bromus tectorum | Bromus secalinus |
| 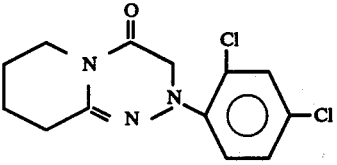 | 1/8<br>1/4<br>1/2 | 0<br>0<br>5C | 0<br>0<br>3C | 3C<br>3C<br>10C | —<br>0<br>10C | 0<br>0<br>3C | 1C<br>2C<br>3C | —<br>2C<br>— | 1C<br>2C<br>3C |
| 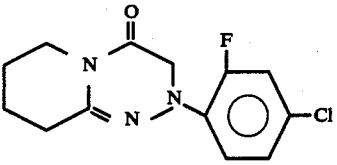 | 1/16<br>1/4 | —<br>4G<br>2C | 0<br>3G<br>1C | 0<br>8G<br>3C | 0<br>0 | 0<br>4C | 0<br>3C | 5C<br>9C | 6C<br>8C |
| 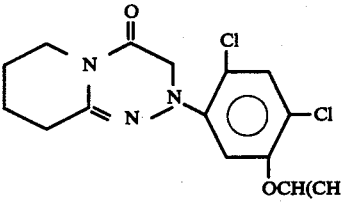 | 1/16<br>1/4 | 1C<br>9C | 2C<br>9C | 9C<br>10C | 0<br>8G | 0<br>9C | 0<br>9C | 7C<br>7C | 2C<br>6C |

Test D

Plastic pots filled with Fallsington sandy loam were planted to soybeans, cotton, alfalfa, corn, rice, wheat, sorghum, cassia (*Cassia tora*), morningglory (*Ipomoea* spp.), jimsonweed (*Datura stramonium*), cocklebur (*Xanthium pensylvanicum*), crabgrass (*Digitaria* spp.), nutsedge (*Cyperus rotundus*), barnyardgrass (*Echinochloa crusgalli*), giant foxtail (*Setaria faberi*) and wild oats (*Avena fatua*). Eighteen days after planting, the young plants and the soil around them were sprayed over-all with the test chemical dissolved in a non-phytotoxic solvent. Fourteen days after treatment, all species were compared to untreated controls and visually rated for response to treatment, as described in Table I. The data are presented in Table IV.

TABLE IV

| Compound | Rate kg/ha | Soybeans | Cassia | Cotton | Morning-glory | Alfalfa | Jimson-weed | Cocklebur | Corn | Crab grass | Rice | Nut-sedge | Barn-yard-grass | Wheat | Giant Foxtail | Wild Oats | Sor-ghum |
|---|---|---|---|---|---|---|---|---|---|---|---|---|---|---|---|---|---|
| | | | | | | | Over-the-Top Soil/Foliage Treatment | | | | | | | | | | |
| 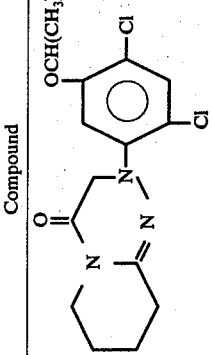 | 0.125<br>0.50 | 4B<br>5B | —<br>— | 9B<br>10B | 6B<br>7B | 0<br>5B | 10B<br>10B | 3B<br>6B | 3C<br>3C | 4C<br>7H | 2C<br>8C | 2C<br>— | 6B<br>7B | 3B<br>3B | 3B<br>8B | 2C<br>5C | 3C<br>5B |
| 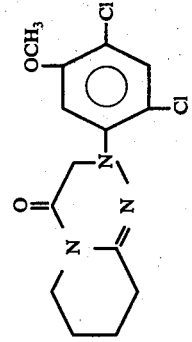 | 0.125<br>0.50 | 4B<br>5B | 2B<br>— | 3B<br>10B | 5B<br>6B | 3B<br>3B | 9B<br>10B | 2B<br>2B | 2C<br>3C | 2H<br>7H | 3C<br>8C | 0<br>2C | 3B<br>9B | 2C<br>3C | 3B<br>9B | 0<br>3C | 3C<br>4B |

What is claimed is:
1. A compound of the formulae:

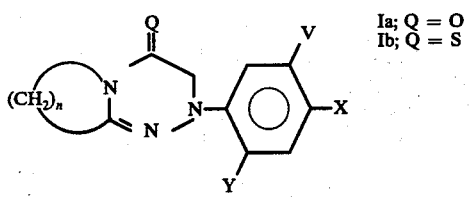

Ia; Q = O (I)
Ib; Q = S

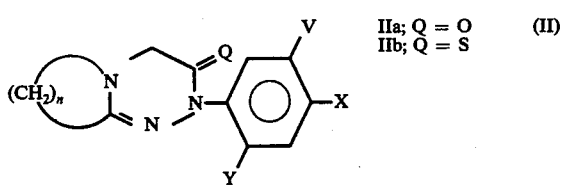

IIa; Q = O (II)
IIb; Q = S wherein:
V is hydrogen, fluorine, chlorine, bromine, methyl or —OR wherein R is alkyl of 1 to 4 carbon atoms;
X is hydrogen, fluorine, chlorine, bromine, cyano, methyl, methoxy or nitro;
Y is hydrogen, fluorine, chlorine, bromine or methyl;
$n$ is 3, 4, or 5; and
Q is oxygen or sulfur.

2. A compound of claim 1 wherein Q is oxygen.
3. A comound of claim 1 wherein V is hydrogen, chlorine, bromine or —OR.
4. A compound of claim 1 wherein X is fluorine, chlorine or bromine.
5. A compound of claim 1 wherein Y is fluorine, chlorine, bromine or methyl.
6. A compound of claim 1 wherein $n$ is 4 or 5.
7. A compound of claim 1 wherein V is hydrogen, chlorine, or —OR.
8. A compound of claim 1 wherein X is chlorine or bromine.
9. A compound of claim 1 wherein Y is fluorine, chlorine or bromine.
10. A compound of claim 1 wherein $n$ is 4.
11. A compound of claim 1 wherein Q is oxygen, V is hydrogen, chlorine or —OR, X is chlorine or bromine, Y is fluorine, chlorine or bromine and $n$ is 4.
12. A compound of claim 1 2-(2,4-dichlorophenyl)-2,3,6,7,8,9-hexahydro-4H-pyrido[2,1-c] [1,2,4]-triazin-4-one.
13. A compound of claim 1 2-(4-chloro-2-fluorophenyl)-2,3,6,7,8,9-hexahydro-4H-pyrido[2,1-c][1,2,4]triazin-4-one.
14. A compound of claim 1 2-(2,4-dichloro-5-methoxyphenyl)-2,3,6,7,8,9-hexahydro-4H-pyrido[2,1-c]triazin-4-one.
15. A compound of claim 1 2-[2,4-dichloro-5-(1-methylethoxy)phenyl]-2,3,6,7,8,9-hexahydro-4H-pyrido[2,1-c][1,2,4]triazin-4-one.
16. A compound of claim 1 2-(2,4-dichlorophenyl)-6,7,8,9-tetrahydro-4H-pyrido[2,1-c][1,2,4]triazin-3[2H]-one.
17. A compound of claim 1 2-(4-chloro-2-fluorophenyl)-6,7,8,9-tetrahydro-4H-pyrido[2,1-c][1,2,4]-triazin-3[2H]-one.
18. A compound of claim 1 2-(2,4-dichloro-5-methoxyphenyl)-6,7,8,9-tetrahydro-4H-pyrido[2,1-c][1,2,4]-triazin-3[2H]-one.
19. A compound of claim 1 2-[2,4-dichloro-5-(1-methylethoxy)phenyl]-6,7,8,9-tetrahydro-4H-pyrido[2,1-c][1,2,4]triazin-3[2H]-one.
20. A composition for the control of undesirable vegetation consisting essentially of a compound of claim 1 and at least one of (a) a surface-active agent, and (b) a solid or liquid diluent.
21. A composition for the control of undesirable vegetation consisting essentially of a compound of claim 2 and at least one of (a) a surface-active agent, and (b) a solid or liquid diluent.
22. A composition for the control of undesirable vegetation consisting essentially of a compound of claim 3 and at least one of (a) a surface-active agent, and (b) a solid or liquid diluent.
23. A composition for the control of undesirable vegetation consisting essentially of a compound of claim 4 and at least one of (a) a surface-active agent, and (b) a solid or liquid diluent.
24. A composition for the control of undesirable vegetation consisting essentially of a compound of claim 5 and at least one of (a) a surface-active agent, and (b) a solid or liquid diluent.
25. A composition for the control of undesirable vegetation consisting essentially of a compound of claim 6 and at least one of (a) a surface-active agent, and (b) a solid or liquid diluent.
26. A composition for the control of undesirable vegetation consisting essentially of a compound of claim 7 and at least one of (a) a surface-active agent, and (b) a solid or liquid diluent.
27. A composition for the control of undesirable vegetation consisting essentially of a compound of claim 8 and at least one of (a) a surface-active agent, and (b) a solid or liquid diluent.
28. A composition for the control of undesirable vegetation consisting essentially of a compound of claim 9 and at least one of (a) a surface active agent and (b) a solid or liquid diluent.
29. A composition for the control of undesirable vegetation consisting essentially of a compound of claim 10 and at least one of (a) a surface-active agent, and (b) a solid or liquid diluent.
30. A composition for the control of undesirable vegetation consisting essentially of a compound of claim 11 and at least one of (a) a surface-active agent, and (b) a solid or liquid diluent.
31. A composition for the control of undesirable vegetation consisting essentially of the compound of claim 12 and at least one of (a) a surface-active agent, and (b) a solid or liquid diluent.
32. A composition for the control of undesirable vegetation consisting essentially of the compound of claim 13 and at least one of (a) a surface-active agent, and (b) a solid or liquid diluent.
33. A composition for the control of undesirable vegetation consisting essentially of the compound of claim 14 and at least one of (a) a surface-active agent, and (b) a solid or liquid diluent.
34. A composition for the control of undesirable vegetation consisting essentially of the compound of claim 15 and at least one of (a) a surface-active agent, and (b) a solid or liquid diluent.
35. A composition for the control of undesirable vegetation consisting essentially of the compound of claim 16 and at least one of (a) a surface-active agent, and (b) a solid or liquid diluent.

36. A composition for the control of undesirable vegetation consisting essentially of the compound of claim 17 and at least one of (a) a surface-active agent, and (b) a solid or liquid diluent.

37. A composition for the control of undesirable vegetation consisting essentially of the compound of claim 18 and at least one of (a) a surface-active agent, and (b) a solid or liquid diluent.

38. A composition for the control of undesirable vegetation consisting essentially of the compound of claim 19 and at least one of (a) a surface-active agent, and (b) a solid or liquid diluent.

39. A method for the control of undesirable vegetation comprising applying to the locus of such undesirable vegetation a herbicidally effective amount of a compound of claim 1.

40. A method for the control of undesirable vegetation comprising applying to the locus of such undesirable vegetation a herbicidally effective amount of a compound of claim 2.

41. A method for the control of undesirable vegetation comprising applying to the locus of such undesirable vegetation a herbicidally effective amount of a compound of claim 3.

42. A method for the control of undesirable vegetation comprising applying to the locus of such undesirable vegetation a herbicidally effective amount of a compound of claim 4.

43. A method for the control of undesirable vegetation comprising applying to the locus of such undesirable vegetation a herbicidally effective amount of a compound of claim 5.

44. A method for the control of undesirable vegetation comprising applying to the locus of such undesirable vegetation a herbicidally effective amount of a compound of claim 6.

45. A method for the control of undesirable vegetation comprising applying to the locus of such undesirable vegetation a herbicidally effective amount of a compound of claim 7.

46. A method for the control of undesirable vegetation comprising applying to the locus of such undesirable vegetation a herbicidally effective amount of a compound of claim 8.

47. A method for the control of undesirable vegetation comprising applying to the locus of such undesirable vegetation a herbicidally effective amount of a compound of claim 9.

48. A method for the control of undesirable vegetation comprising applying to the locus of such undesirable vegetation a herbicidally effective amount of a compound of claim 10.

49. A method for the control of undesirable vegetation comprising applying to the locus of such undesirable vegetation a herbicidally effective amount of a compound of claim 11.

50. A method for the control of undesirable vegetation comprising applying to the locus of such undesirable vegetation a herbicidally effective amount of the compound of claim 12.

51. A method for the control of undesirable vegetation comprising applying to the locus of such undesirable vegetation a herbicidally effective amount of the compound of claim 13.

52. A method for the control of undesirable vegetation comprising applying to the locus of such undesirable vegetation a herbicidally effective amount of the compound of claim 14.

53. A method for the control of undesirable vegetation comprising applying to the locus of such undesirable vegetation a herbicidally effective amount of the compound of claim 15.

54. A method for the control of undesirable vegetation comprising applying to the locus of such undesirable vegetation a herbicidally effective amount of the compound of claim 16.

55. A method for the control of undesirable vegetation comprising applying to the locus of such undesirable vegetation a herbicidally effective amount of the compound of claim 17.

56. A method for the control of undesirable vegetation comprising applying to the locus of such undesirable vegetation a herbicidally effective amount of the compound of claim 18.

57. A method for the control of undesirable vegetation comprising applying to the locus of such undesirable vegetation a herbicidally effective amount of the compound of claim 19.

* * * * *